(12) United States Patent
Brigham

(10) Patent No.: US 7,611,399 B2
(45) Date of Patent: Nov. 3, 2009

(54) HANDS-FREE BREAST PUMPING SUPPORT DEVICE

(76) Inventor: Merilee Brigham, 6003 Corliss Ave. North, Seattle, WA (US) 98103

( * ) Notice: Subject to any disclaimer, the term of this patent is extended or adjusted under 35 U.S.C. 154(b) by 48 days.

(21) Appl. No.: 11/385,248

(22) Filed: Mar. 20, 2006

(65) Prior Publication Data

US 2006/0211336 A1 Sep. 21, 2006

Related U.S. Application Data

(60) Provisional application No. 60/663,896, filed on Mar. 21, 2005.

(51) Int. Cl.
*A41C 3/00* (2006.01)
(52) U.S. Cl. .......................... 450/36; 604/74
(58) Field of Classification Search ................ 450/36, 450/37; 2/104; 604/118, 119, 73–76, 315, 604/320, 322, 323, 326, 346; 601/14, 6; 54/20, 58, 59; 119/14.43, 14.47, 14.48, 14.49, 119/14.51
See application file for complete search history.

(56) References Cited

U.S. PATENT DOCUMENTS

| | | | |
|---|---|---|---|
| 5,459,903 A * | 10/1995 | Treacy ...................... 24/3.13 |
| 5,611,118 A * | 3/1997 | Bibbee ........................ 24/298 |
| 6,026,548 A | 2/2000 | Jackson | |
| 6,092,897 A * | 7/2000 | Smerdon, Jr. ............... 351/157 |
| 6,764,177 B1 * | 7/2004 | Chisolm .................... 351/157 |
| 6,764,377 B2 | 7/2004 | Gillan | |
| 6,941,619 B2 * | 9/2005 | Mackay et al. ................ 24/3.3 |
| 6,974,361 B2 * | 12/2005 | Cravaack et al. .............. 450/36 |
| 6,988,930 B2 * | 1/2006 | Gillan ......................... 450/36 |

OTHER PUBLICATIONS

"Hands-Free Pumping Products," n.d., 6 pages.

* cited by examiner

*Primary Examiner*—Gloria Hale
(74) *Attorney, Agent, or Firm*—Christensen O'Connor Johnson Kindness PLLC

(57) ABSTRACT

A hands-free breast pumping support device (20) generally includes a strap (22) having first and second end portions (24 and 26), and first and second fasteners (28 and 30) coupled to the strap first and second end portions. The first and second fasteners are operable to be releasably connected to a garment (32) to support at least one breast pumping device (100) coupled to a breast (102) or releasably connected to the strap to form a loop of selectable size (34) to support at least one breast pumping device coupled to a breast.

14 Claims, 6 Drawing Sheets

HANDS-FREE BREAST PUMPING SUPPORT DEVICE

CROSS-REFERENCE TO RELATED APPLICATION

This application claims the benefit of U.S. Provisional Application No. 60/663,896, filed Mar. 21, 2005, the benefit of which is hereby claimed under 35 U.S.C. § 119 and is incorporated herein by reference.

TECHNICAL FIELD

Embodiments of the present disclosure relate generally to breast pumping support devices and, more specifically, to hands-free breast pumping support devices.

BACKGROUND

Breast milk is the recommended diet for children during the first twelve months of their lives. For many mothers, breastfeeding for twelve months after childbirth is difficult. One of the common difficulties is that the mother is often employed outside the home and/or has periods of the day during which she is separated from her child. In order to provide breast milk to her child while she is away, the mother must express her milk and store the milk for use with a bottle.

The expression or pumping of breast milk using a breast pump to stimulate and maintain an adequate milk supply is very time consuming. It renders the mother stationary during a pumping session, holding a breast pumping device (or devices) in place with either one or two hands. Many mothers find that the immobility required to hold the breast pump components in place is a burdensome part of the breast pumping process.

While there are some hands-free breast pumping support devices currently available in the marketplace, these devices are expensive, bulky, uncomfortable, and/or difficult to use. Hence, there exists a need for a hands-free breast pumping support device which is economical, easy to transport, comfortable, and easy to use.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with one embodiment of the present disclosure, a hands-free breast pumping support device is provided. The support device includes a strap having first and second end portions, and first and second fasteners coupled to the strap first and second end portions. The first and second fasteners are operable to be releasably connected to a garment to support at least one breast pumping device coupled to a breast, or releasably connected to the strap to form a loop of selectable size to support at least one breast pumping device coupled to a breast.

In accordance with another embodiment of the present disclosure, a method of hands-free breast pumping is provided. The method includes coupling at least one breast pumping device to a breast. The method further includes positioning a support device including a strap having first and second end portions behind a neck of a user and downwardly along the front of the user's torso. The support device further includes first and second fasteners coupled to the first and second end portions, the first and second fasteners configured to be releasably attachable to a garment or the strap. The method further includes attaching the first and second fasteners to a garment to support at least one breast pumping device, or attaching the first and second fasteners to the strap to form a loop of selectable size to support at least one breast pumping device.

DESCRIPTION OF THE DRAWINGS

The foregoing aspects and many of the attendant advantages of this disclosure will become more readily appreciated by reference to the following detailed description, when taken in conjunction with the accompanying drawings, wherein.

DETAILED DESCRIPTION

Figure 1:
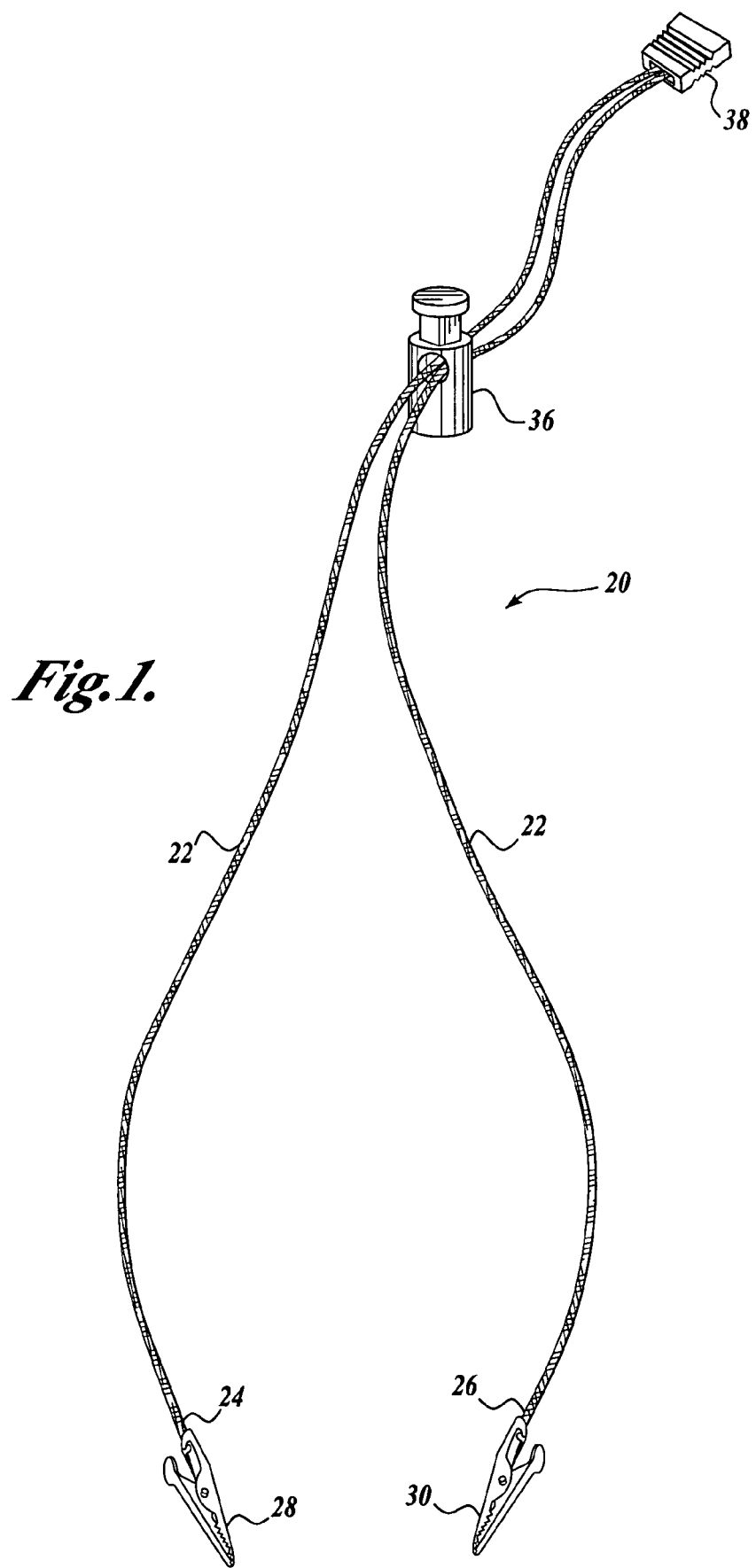
FIG. 1 is a perspective view of an exemplary embodiment of a hands-free breast pumping support device according to various aspects of the present disclosure.

Embodiments of the present disclosure are generally directed to a hands-free breast pumping support device and methods of hands-free breast pumping. A hands-free breast pumping support device 20 constructed in accordance with one embodiment of the present disclosure may be best understood by referring to FIG. 1. The support device 20 generally includes a strap 22 having first and second end portions 24 and 26, and first and second fasteners 28 and 30 coupled to respective first and second end portions 24 and 26 of the strap.

The fasteners 28 and 30 are designed and configured to be releasably connected to a garment 32, such as a nursing bra (see FIG. 2), or to the strap 22 itself to form a closed loop 34 of selectable size (see FIG. 3), such that the support device 20 can support at least one breast pumping device 100 when it is coupled to a user's breast 102. In other orientations, the support device 20 can also support two breast pumping devices 100 coupled to both of the user's breasts 102 (see FIGS. 4-6).

A breast pumping device 100 in accordance with various aspects of the present disclosure is generally any suitable structure for coupling to a lactating human breast to express and collect milk. In general, the device 100 includes a breast shield 110 that is dimensioned and shaped to receive a portion of a breast 102 and that includes a central opening 112. The breast pumping device 100 further includes a receiving tube 114 in fluid communication with the interior of the breast shield 110 through the central opening 112, a milk container 116, and a venturi channel 118.

In general, air is directed from an external pumping device (not shown) to the venturi channel 118 and back again to the external pumping device via a hose (not shown), which contains forward and reverse air. The venturi channel 118 is shaped internally to develop suction in the receiving tube 114 as a result of that air flow, in accordance with the Venturi effect.

In order to maintain a suction fit between the breast shield 110 and the user's breast 102, the breast pumping device 100 must be maintained in a "supported position" relative to the user's body. Although a desired supported position may be different for different body-types, for generally good results, the breast pumping device 100 is maintained such that the receiving tube 114 is substantially perpendicular to the front of a user's torso at the breast 102. The support device 20 of the present disclosure can be adapted for use with a variety of different battery and/or electric breast pumping devices.

The support device 20 of the present disclosure helps maintain the breast pumping device 100 in a desired supported position, such that the user need not hold the breast pumping device 100 in the desired position with her hands. In that regard, when the support device 20 is connected to a garment 32, the support device 20 supports the garment 32 such that the garment 32 provides lifting support underneath the breast pumping device 100 to maintain the desired supported position. Specifically, the garment 32 supports the receiving tube 114 in a supported or substantially perpendicular position relative to the front of the user's torso at the breast 102. As discussed in greater detail below with reference to FIGS. 2, 4, and 5, the support device 20 is adaptable for use with a variety of styles of garments or nursing bras.

When the support device 20 is connected to itself, the support device 20 itself provides support to the underside of the receiving tube 114 to achieve and maintain its supported or substantially perpendicular position relative to the front of the user's torso at the breast 102.

Various aspects of the support device 20 will now be discussed in greater detail. In that regard, the first and second fasteners 28 and 30 may be any suitable releasable fasteners known and used in the art that will remain fastened to the garment 32 or the strap 22 itself when the garment 32 or the strap 22 is under a load associated with at least one, and up to two, breast pumping devices 100. As non-limiting examples, suitable releasable fasteners include snaps, buttons, clips (such as spring clips and other clips), pins (such as safety pins and other pins), hook and loop fasteners, and clamps. As another non-limiting example, and as illustrated in FIGS. 1-6, the first and second fasteners 28 and 30 are alligator clamps. Such fasteners are designed and configured to grip the garment 32 or the strap 22 with sufficient force to remain fastened under the associated loads.

The strap 22 may be of any length of material suitable for suspending the load associated with either one or two breast pumping devices 100 behind a neck 104 of a user. As non-limiting examples, the material of the strap 22 can have a cross section that is thin and flat (such as a camera strap or a guitar strap), round (such as a soft-core cord), or braided. In addition, the strap 22 may be made of a flexible or elastic material that stretches when under a load. As a non-limiting example, the strap 22 is a round elastic cord surrounded by a braided outer covering.

In one embodiment of the present disclosure, the strap 22 has an adjustable length. As a non-limiting example, the support device 20 further includes a length adjustment device 36. As illustrated in the embodiments of FIGS. 1 and 3-6, the length adjustment device 36 is a spring-loaded push-release locking device for securing a strap, which provides quick release for ease of adjustment. The support device 20 may further include one or more tabs 38 to aid in gripping the strap 22 for manually adjusting the strap 22 length and/or to impede disengagement of the strap 22 from the length adjustment device 36.

As other non-limiting examples, other length adjustment devices may include any of a variety of belt buckle systems, ties, hook and loop adjustment devices, adjustable clasps, or any other length adjustment devices known and used in the art that will hold their length adjustment position under a load associated with one or two breast pumping devices 100. In addition, as a non-limiting example, the strap 22 may comprise multiple segments which are coupled together, for example, two segments which are attached by being tied or otherwise coupled to behind the neck 104 of the user to form a strap 22 of a certain length.

The support device 20 may further include a comfort pad 46 (see FIG. 2), which is attachable to at least a portion of the strap 22 that extends behind the neck 104 of the user. Such a comfort pad may be of any suitable material and construction known and used in the art for providing comfort between a strap and the neck 104 of the user.

Figure 4:
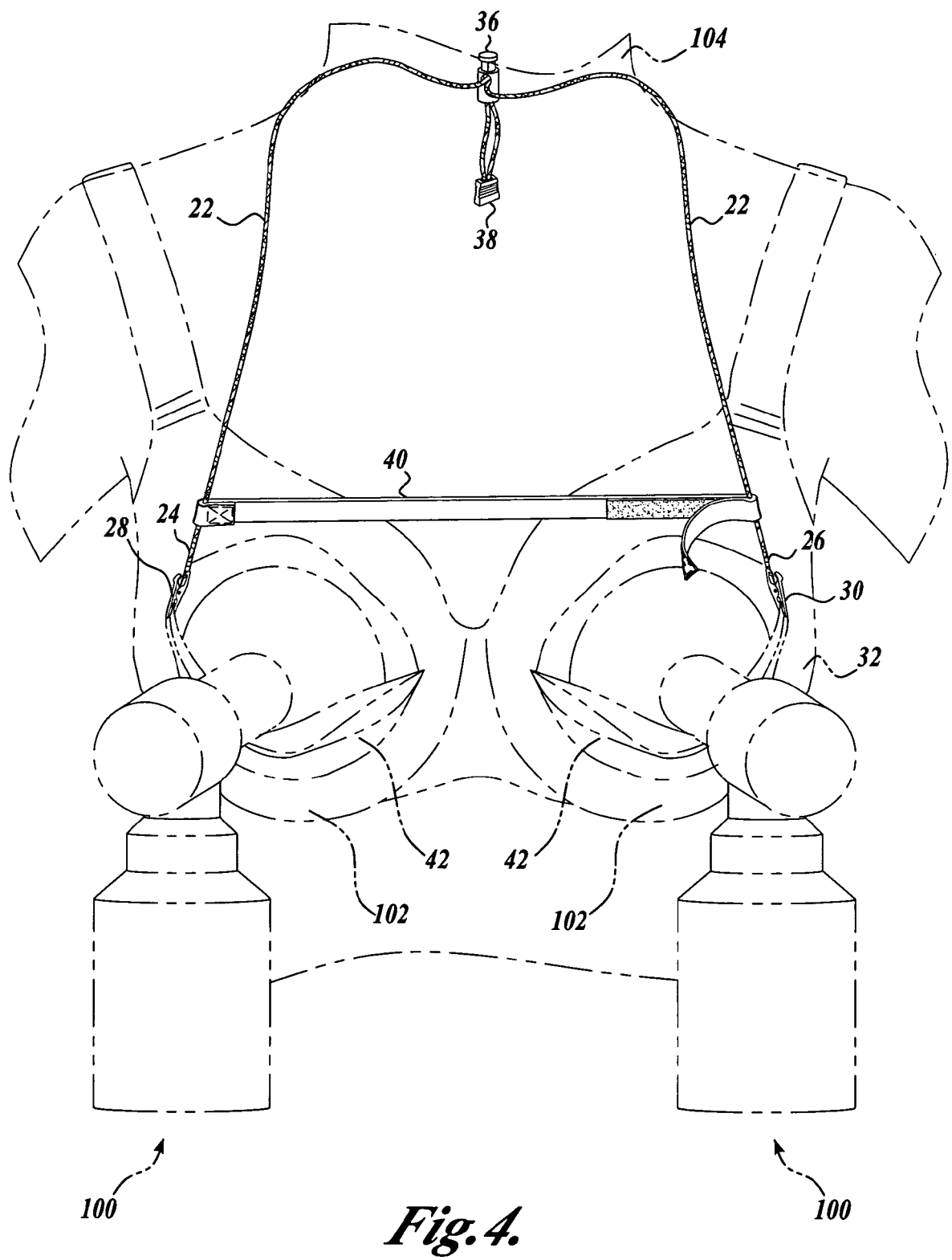
FIG. 4 is a perspective view of the support device of FIG. 1 in a third orientation.

Referring to FIG. 4, the support device 20 may further include a chest strap 40 extending across a chest 106 of the user and positioned between two points on the strap 22 near or spaced from the first and second end portions 24 and 26 of the strap 22 when the first and second fasteners 28 and 30 are attached to either a garment 34 or the strap 22. The chest strap 40 interconnects the strap at locations spaced from the first and second end portions 24 and 26. Such a chest strap 40 adds tension to the strap 22 and may help maintain the breast pumping device(s) 100 and the support device 20 in "supported positions" relative to the user's body.

In the illustrated embodiment of FIG. 4, the chest strap 40 is a hook and loop fastening strap that extends across the chest 106 of the user between the first and second end portions 24 and 26 of the strap 22. However, it should be appreciated that other chest straps 40 known and used in the art are also within the scope of the disclosure. As a non-limiting example, a second support device 20 may be used as a chest strap 40.

The operation of the system will now be described with reference to FIGS. 2-6, in which there are shown multiple non-limiting examples of orientations for the hands-free breast pumping support device 20 depicted in the exemplary embodiment of FIG. 1. As discussed above, the support device 20 is designed and configured to be releasably connected to a garment 32 (such as a nursing bra) or to the strap 22 itself to form a closed loop 34 of selectable size, such that the support device 20 can support at least one breast pumping device 100 as it is coupled to the breast 102 of the user. In the illustrated orientations of FIGS. 2 and 3, the support device 20 supports only one breast pumping device 100 as it is coupled to the user's breast 102. However, in the illustrated orientations of FIGS. 4-6, the support device 20 supports two breast pumping devices 100 as they are coupled to the user's breasts 102.

Figure 2:
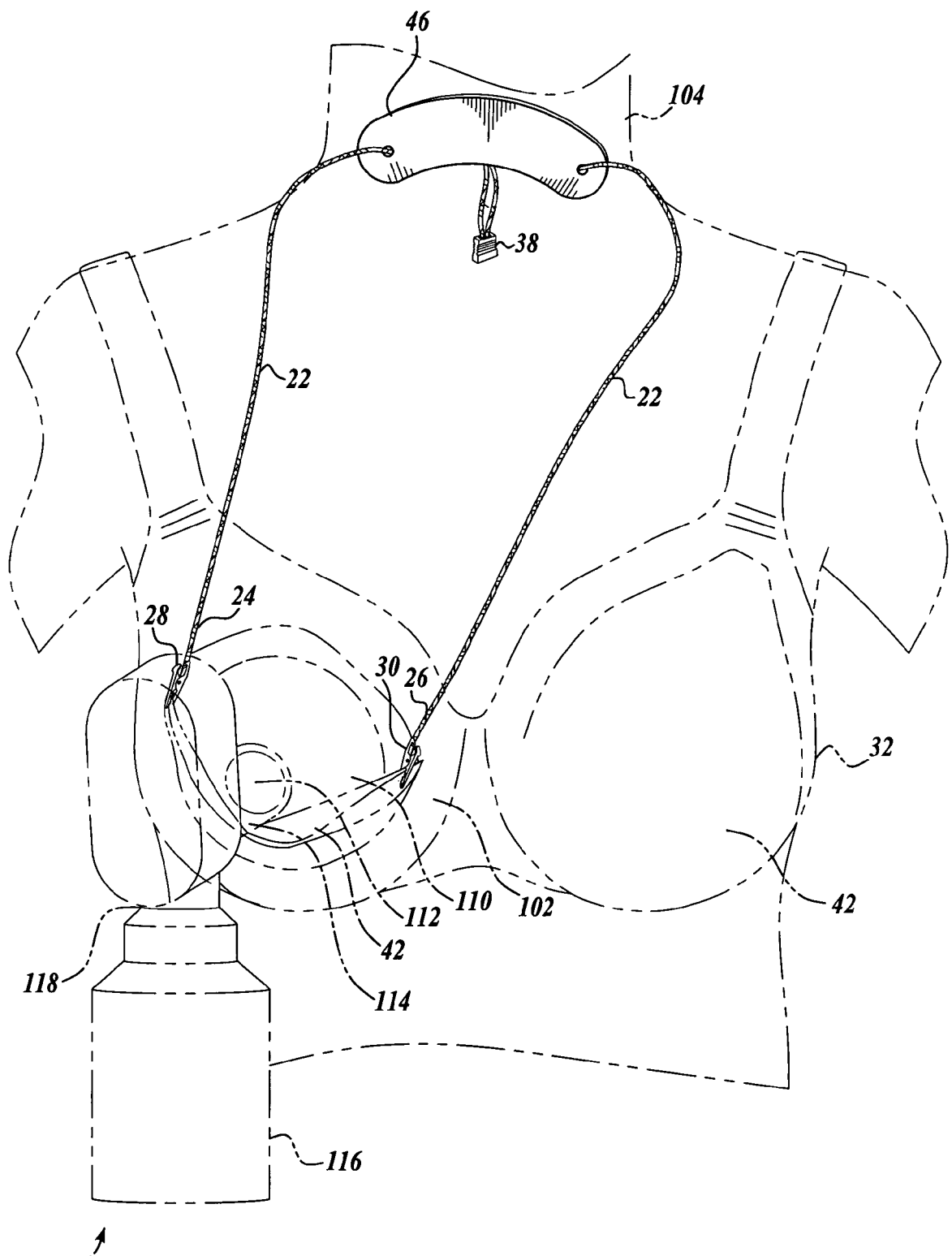
FIG. 2 is a perspective view of the support device of FIG. 1 in a first orientation.

Referring to FIG. 2, the support device 20 is shown in a first orientation. In this orientation, the strap 22 is positioned behind the user's neck and downwardly along the front of the user's torso to terminate at the first and second end portions 24 and 26. The first and second fasteners 28 and 30 coupled to respective first and second end portions 24 and 26 are attachable to two sides of an open-able panel 42 on one cup of the nursing bra 32. When properly adjusted in this orientation, the support device 20 provides lifting support to the lower portion of the open-able panel 42 of the nursing bra 32. In that regard, the support device 20 supports the panel 42 such that the panel 42 provides support to the underside of the receiving tube 114 to maintain the receiving tube 114 in its supported or substantially perpendicular position relative to the front of the user's torso at the breast 102.

In the first orientation, as well as in any of the following orientations, the support device 20 transfers the load of the breast pumping device 100 to the support device 20 and the user's neck 104. In should be appreciated that in each orientation, the elevation and orientation of the breast pumping device 100 relative to the breast 102 can be adjusted by adjusting either the positioning of the first and second fasteners 28 and 30 or by adjusting the length of the strap 22 by, for example, repositioning the length adjustment device 36 relative to the strap 22. It should further be appreciated that in each orientation two or more support devices 20 may be used in concert in a manner similar to the single support device 20 application. Two or more support devices 20 will provide reinforcement or extra support for the user.

Figure 3:
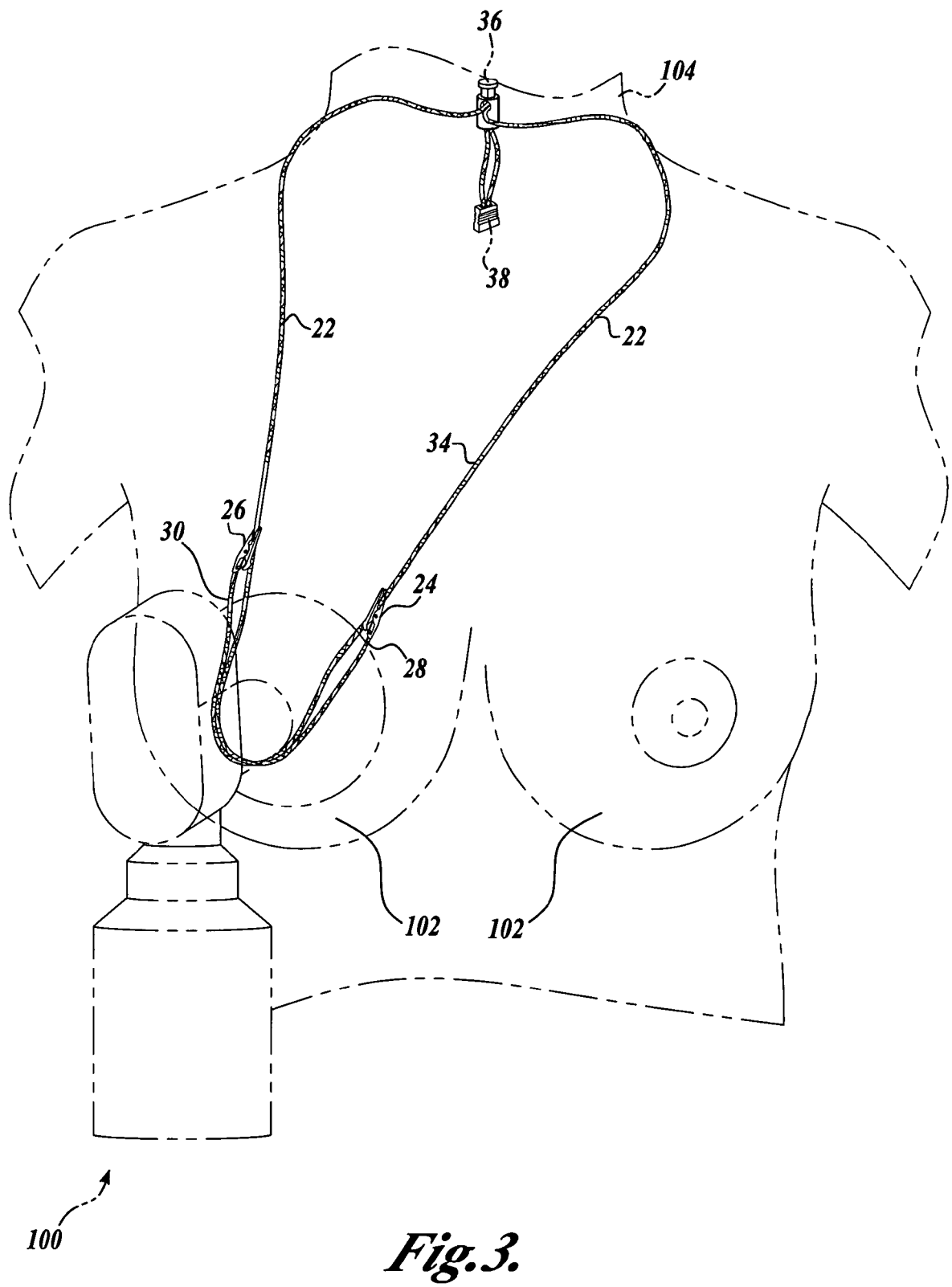
FIG. 3 is a perspective view of the support device of FIG. 1 in a second orientation.
Figure 6:
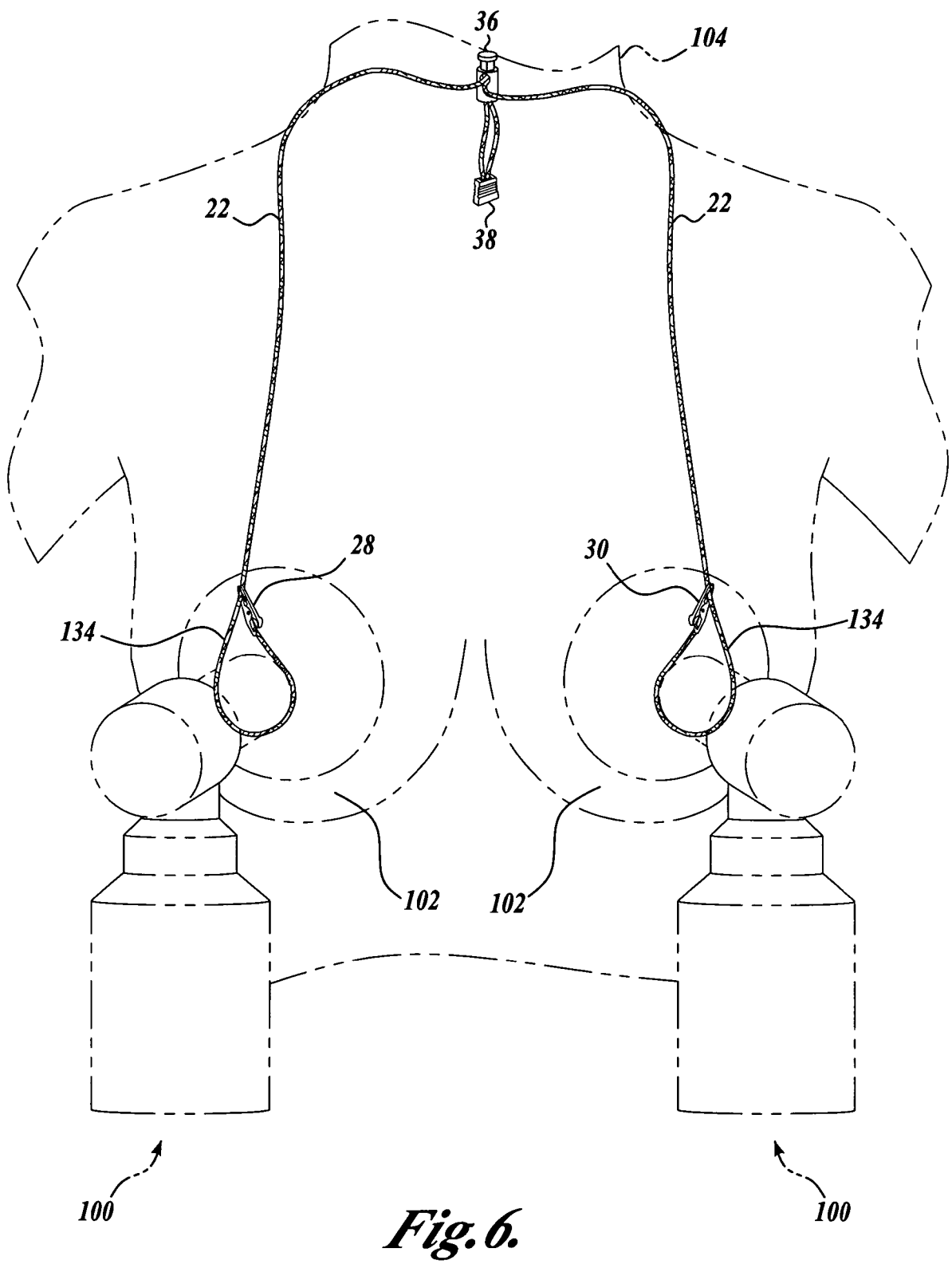
FIG. 6 is a perspective view of the support device of FIG. 1 in a fourth orientation.

As best seen in FIGS. 3, and 6, the support device 20 can be used without a nursing bra. In should be appreciated that when the support device 20 is used without a nursing bra, the elevation and orientation of the breast pumping device 100 relative to the breast 102 can be adjusted by adjusting the loop 34 size or by adjusting the length of the strap 22 by, for example, repositioning the length adjustment device 36 relative to the strap 22.

Referring to FIG. 3, the strap 22 is again positioned behind the user's neck 104 and downwardly along the front of the user's torso. However, in this second orientation the first and second fasteners 28 and 30 are each attached to the strap 22 adjacent the opposite end portions 26 and 24 of the strap 22 to form one closed loop 34 with the strap 22. When properly adjusted in this orientation, the support device 20 provides lifting support to the underside of the receiving tube 114 to maintain the receiving tube 114 in its supported or substantially perpendicular position.

When used with a garment, one advantage of the support device 20 of the present disclosure is that is can be used with multiple styles of garments or nursing bras 32, including, but not limited to, "shoulder-hook" or "center-snap" style nursing bras. As described below with reference to FIGS. 4 and 5, the positioning of the first and second fasteners 28 and 30 on the garment is dependent upon the style of garment being used.

Figure 5:
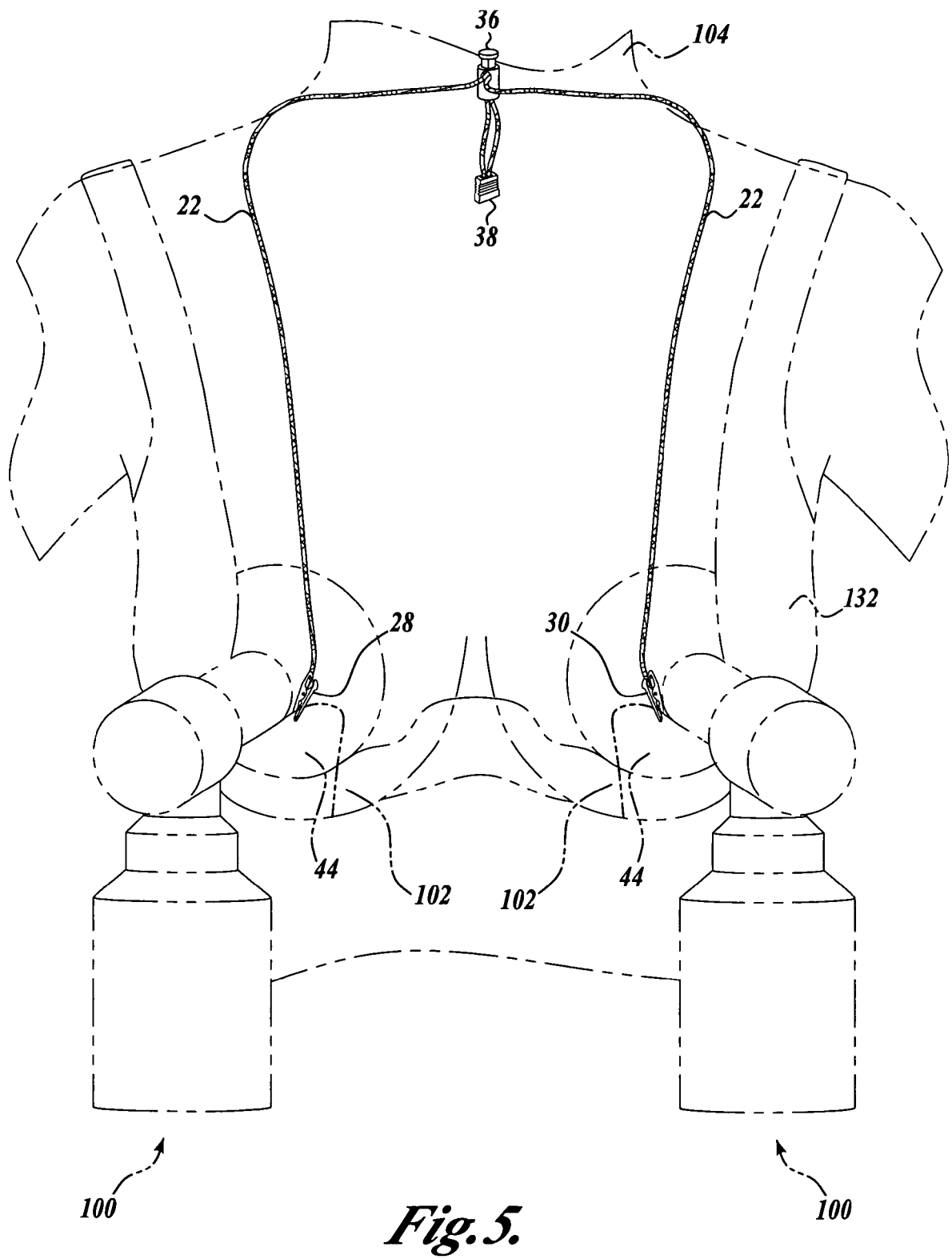
FIG. 5 is a perspective view of the support device of FIG. 1 in a fourth orientation.

Referring to FIGS. 4 and 5, the support device 20 is shown in third and forth orientations. In these orientations, the strap 22 is again positioned behind the user's neck 104 and downwardly along the front of the user's torso. As best seen in FIG. 4 in the third orientation, the first and second fasteners 28 and 30 are attached to the outer sides of two open-able panels 42 on both cups of the "shoulder-hook" style nursing bra 32. When properly adjusted in this orientation, the support device 20 provides lifting support to the lower portions of the open-able panels 42 of the nursing bra 32. In that regard, the support device 20 supports the panels 42 such that the panels 42 provide support underneath the receiving tubes 114 to maintain the receiving tubes 114 in their supported or substantially perpendicular positions.

As seen in FIG. 5 in the fourth orientation, the first and second fasteners 28 and 30 are attached to the inner sides of two open-able panels 44 on both cups of the "center-snap" style nursing bra 132. When properly adjusted in this orientation, the support device 20 provides lifting support to the lower portions of the open-able panels 44 of the nursing bra 132. In that regard, the support device 20 supports the panels 44 such that the panels 44 provides support underneath the receiving tubes 114 to maintain the receiving tubes 114 in their supported or substantially perpendicular positions.

Referring to FIG. 6, the support device 20 is shown in a fifth orientation, similar to the orientation shown in FIG. 3 in that the support device 20 is positioned without the use of a nursing bra. In this fifth orientation, the strap 22 is again positioned behind the user's neck and downwardly along the front of the user's torso. The first and second fasteners 28 and 30 are each attached to the strap 22 near the same respective end portions 24 and 26 of the strap 22 to form two closed loops 134 with the strap 22. When properly adjusted in this orientation, the support device 20 provides lifting support to the undersides of the receiving tubes 114 to maintain the receiving tubes 114 in their supported or substantially perpendicular positions.

While illustrative embodiments have been illustrated and described, it will be appreciated that various changes can be made therein without departing from the spirit and scope of the present disclosure.

The embodiments of the disclosure in which an exclusive property or privilege is claimed are defined as follows:

1. A method of hands-free breast pumping, comprising:
   (a) coupling at least one breast pumping device to a breast;
   (b) positioning a support device strap having a central portion for placement behind a neck of a user and having first and second strap end portions that extend downwardly along the front of the user's torso, the support device strap further comprising first and second fasteners, the first and second fasteners each having a first fastener portion permanently coupled to the first and second strap end portions and a second fastener portion configured to be releasably attachable to the strap itself, wherein the first and second fasteners are selected from the group consisting of clips and clamps; and
   (c) attaching the second fastener portion of the first fastener to the strap itself at a point on the strap that is located between the central portion and the first end portion to form a first loop of selectable size, the selectable size being based on the placement of the first fastener on the strap between the central portion and the first end portion, wherein the first loop of selectable size is sized and located to encircle a portion of the at least one breast pumping device to support at least a portion of the at least one breast pumping device coupled to the breast.

2. The method of claim 1, wherein the strap is a flexible strap.

3. The method of claim 1, further comprising adjusting a length of the strap.

4. The method of claim 1, further comprising positioning a comfort pad behind the neck of the user, wherein the comfort pad is attachable to the strap at a portion of the strap that extends behind the neck of the user.

5. The method of claim 1, further comprising attaching a chest strap interconnecting the strap at locations spaced from the first and second end portions of the strap.

6. A method of hands-free breast pumping, comprising:
   (a) coupling at least one breast pumping device to a breast;
   (b) positioning a support device strap having a central portion for placement behind a neck of a user and having first and second strap end portions that extend downwardly along the front of the user's torso, the support device strap further comprising first and second fasteners, the first and second fasteners each having a first fastener portion permanently coupled to the first and second strap end portions and a second fastener portion configured to be releasably attachable to the strap itself, wherein the first and second fasteners are selected from the group consisting of clips and clamps;
   (c) attaching the second fastener portion of the first fastener to the strap itself at a point on the strap that is located between the central portion and the first end portion to form a first loop of selectable size, the selectable size being based on the placement of the first fastener on the strap between the central portion and the first end portion, wherein the first loop of selectable size is sized and located to encircle a portion of the at least one breast pumping device to support at least a portion of the at least one breast pumping device coupled to the breast; and (d) attaching a chest strap to the strap, wherein the chest strap is attached along the strap at two or more locations, the locations being spaced from the first and second end portions of the strap and between the central portion and the first and second end portion of the strap, and wherein the chest strap adds tension to the strap and maintains the at least one breast pumping device in a supported position.

7. The method of claim 1, further comprising attaching the other of the second fastener portions of the first and second fasteners to a garment.

8. The method of claim 1, further comprising coupling a second breast pumping device to a breast and attaching the other of the second fastener portions of the first and second fasteners to the strap to form a second loop of selectable size, wherein the second loop of selectable size encircles a portion of a second breast pumping device to support the second breast pumping device coupled to the breast.

9. The method of claim 6, further comprising attaching the other of the second fastener portions of the first and second fasteners to a garment.

10. The method of claim 6, further comprising coupling a second breast pumping device to a breast and attaching the other of the second fastener portions of the first and second fasteners to the strap to form a second loop of selectable size, wherein the second loop of selectable size encircles a portion of a second breast pumping device to support the second breast pumping device coupled to the breast.

11. A method of hands-free breast pumping, comprising:

(a) coupling at least one breast pumping device to a breast of a user, wherein the user is wearing a garment adaptable to be pulled away from the front of the user's torso to provide access to the user's breasts;

(b) positioning a support device strap having a central portion for placement behind a neck of a user and having first and second strap end portions that extend downwardly along the front of the user's torso, the support device strap further comprising first and second fasteners, the first and second fasteners each having a first fastener portion permanently coupled to the first and second strap end portions and a second fastener portion configured to be releasably attachable to the garment, wherein the first and second fasteners are selected from the group consisting of clips and clamps;

(c) positioning the garment such that it can be used to support components of the at least one breast pumping device; and (d) attaching the first and second fasteners to the garment at a point on the garment so as to use the garment and the strap to form a loop of selectable size, the selectable size being based on the placement of the first and second fasteners on the garment, wherein the loop of selectable size is sized and located to encircle and to support components of the at least one breast pumping device coupled to the breast.

12. The method of claim 11, wherein the first and second fasteners are selected from the group consisting of clips-and clamps.

13. The method of claim 1, further comprising attaching the second fastener portion of the second fastener to the strap itself at a point on the strap that is located between the central portion and the second end portion to form a first loop of selectable size, such size being based on the placement of the second fastener on the strap between the central portion and the first end portion, wherein the first loop of selectable size is sized and located to encircle a portion of the at least one breast pumping device to support at least a portion of the at least one breast pumping device coupled to the breast.

14. The method of claim 6, further comprising attaching the second fastener portion of the second fastener to the strap itself at a point on the strap that is located between the central portion and the second end portion to form a first loop of selectable size, such size being based on the placement of the second fastener on the strap between the central portion and the first end portion, wherein the first loop of selectable size is sized and located to encircle a portion of the at least one breast pumping device to support at least a portion of the at least one breast pumping device coupled to the breast.

* * * * *

UNITED STATES PATENT AND TRADEMARK OFFICE
CERTIFICATE OF CORRECTION

| | | |
|---|---|---|
| PATENT NO. | : 7,611,399 B2 | Page 1 of 1 |
| APPLICATION NO. | : 11/385248 | |
| DATED | : November 3, 2009 | |
| INVENTOR(S) | : Merilee Brigham | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 48 days.

Signed and Sealed this
Twenty-ninth Day of March, 2011

David J. Kappos
*Director of the United States Patent and Trademark Office*